United States Patent [19]

Guenther

[11] Patent Number: 5,385,145
[45] Date of Patent: Jan. 31, 1995

[54] INVASIVE BLOOD PARAMETER PROBE TO BE INTRODUCED INTO A CATHETER

[75] Inventor: Martin Guenther, Wildberg, Germany

[73] Assignee: Hewlett-Packard Company, Palo Alto, Calif.

[21] Appl. No.: 181,389

[22] Filed: Jan. 13, 1994

Related U.S. Application Data

[63] Continuation of Ser. No. 45,622, Apr. 9, 1993, abandoned.

[30] Foreign Application Priority Data

Apr. 11, 1992 [EP]  European Pat. Off. ............ 92106320

[51] Int. Cl.⁶ .............................................. A61B 5/00
[52] U.S. Cl. .................................. 128/634; 128/636; 128/637
[58] Field of Search ................................ 128/633–635, 128/637, 668, 636; 604/171–172

[56] References Cited

U.S. PATENT DOCUMENTS

| | | |
|---|---|---|
| 3,249,103 | 5/1966 | Woodhouse . |
| 3,757,771 | 9/1973 | Ruegg et al. . |
| 3,981,297 | 9/1976 | Dunn et al. . |
| 4,795,434 | 1/1989 | Kujawski ..................... 128/634 X |
| 4,951,669 | 8/1990 | Maxwell et al. ............... 128/634 X |

FOREIGN PATENT DOCUMENTS 0311427  4/1989  European Pat. Off. .

Primary Examiner—Angela D. Sykes

[57] ABSTRACT

An invasive blood parameter probe includes a flexible pressure tube which surrounds the sterile probe portion. When the pressure tube is stretched, the proximal probe tip slips into the pressure tube. Pressure tube is held in its elongated position by means of an—e.g. U-shaped—spanning member against which a Y-connector and a threaded sleeve abut. A container may now be replaced, under sterile conditions, by a catheter.

6 Claims, 5 Drawing Sheets

INVASIVE BLOOD PARAMETER PROBE TO BE INTRODUCED INTO A CATHETER

This is a continuation, of application Ser. No. 08/045,622, filed Apr. 9, 1993, now abandoned.

FIELD OF THE INVENTION

The present invention relates to the field of invasive blood parameter measurement, in particular to invasive blood gas monitoring. More specifically, the invention relates to a method for sterile introduction of an invasive blood parameter probe into a catheter.

BACKGROUND OF THE INVENTION

Probes for the invasive measurement of blood parameters consist—in one embodiment—of at least one sensor comprising an optical fiber, wherein said fiber ends up with a gel zone containing a dye. The optical density or another optical parameter of the dye varies with the blood parameter (such as pH, $pO_2$ or $pCO_2$) to be measured. On the other side of the dye-containing gel, a reflector is positioned. The end of the fiber, the gel and the reflector are surrounded by a semi-permeable envelope (for example, a hydrogen ion permeable envelope in the case of a pH sensor) to keep the gel in place.

Light from this optical fiber passes the dye-containing gel, is reflected by said reflector, passes the gel again and is transmitted through the optical fiber to an appropriate detector which measures light attenuation or changes in other optical parameters caused by the dye. This attenuation or change is a function of the blood parameter to be measured, and the relation between attenuation, absorbance or the change of another optical parameter and the blood parameter is well-known.

Such a probe can be introduced into the patient's artery to measure—depending on the dye and/or the selected semi-permeable envelope—various blood parameters such as pH, $pO_2$ or $pCO_2$.

For further details of invasive blood parameter monitoring, reference is made to several patent documents which describe this technology in detail, for example, EP-A-279 004, U.S. Pat. No. 4,900,381, EP-A-336 986, EP-A-336 984, EP-A-336 985, EP-A-53 599 and EP-A-471 861, all of which are hereby incorporated by reference herein.

Such an optical probe is designed for introduction into a blood vessel of a patient. Introduction is usually performed by advancing the probe through a catheter.

It will be understood that it is a major requirement in such an application that the portion of the probe intended for blood contact is kept sterile. That is, the probe tip and other parts of the probe establishing direct blood contact may not be handled with the fingers, nor come into contact with any other non-sterile components or parts of the body. If such happens, the probe is not further useful for any medical application. Most commonly, it will be thrown away.

It is, of course, possible to keep the probe in a sterile container. However, the major problem occurs when the probe is introduced into the catheter. As soon as the sterile packaging of the probe is removed, it has to be introduced into the distal opening of the catheter (which has a very small diameter).

It will be understood that this complicated handling process may give a rise to faults. In particular, an inaccuracy upon introduction of the probe may cause physical contact between the sterile part of the probe and other non-sterile equipment, such as an extracorpular part of the catheter, a table, a part of the human body (such as the fingers of the assembling person), and the like.

Further inconveniences are caused by the fact that both the probe and the catheter may only be touched at non-sterile portions, or at their packaging. Imagine, for example, a probe and a catheter, both contained in sterile plastic bags. The assembling person may well be able to remove part of the catheter's plastic bag, and to hold the catheter at the portion still surrounded by the packaging. However, the problem now arises how to remove part of the probe's plastic bag with one hand—the other hand still holds the catheter, which may not be put down, in order to keep it sterile. One can, of course, try to hold the partially opened catheter between, let us say, the middle finger and the ring finger of the left hand, and try to open the probe's plastic bag with the thumb and the forefinger of the same hand (while the right hand holds the plastic bag of the probe). However, it is apparent that this is no perfect solution, and that the sterile part of the catheter may easily come into contact with non-sterile things or bodies.

Thus, the probe cannot be reliably introduced into the catheter by a single person, and this method is actually seldom used in clinical practice. Instead, two persons helping each other during assembly will be required (wherein one persons handles the non-sterile parts, and the other person, wearing sterile gloves, handles the sterile components, for example, on a sterile cloth).

Another problem of the method discussed above is that complicated packaging technology is required, e.g., plastic bags for all (movable) sterile components. It should also be noted that such plastic bags imply additional risk for the patient, as the plastic bag may accidentally be damaged. If such accidental damage is not observed by medical personnel, non-sterile parts come into contact with the patient's blood.

Yet another problem is that hermetic sealing between the probe and the catheter is not easy. It is evident that such sealing is required to keep the probe, as well as the interior of the catheter, in a sterile condition.

A further problem encountered is that the probe has to be recalibrated from time to time, and that the catheter has to be flushed, in order to avoid clot formation.

SUMMARY OF THE INVENTION

It is thus a major object of the present invention to provide an improved method for sterile introduction of an invasive blood parameter probe into a catheter.

According to the invention, the sterile part of the probe is surrounded by flexible (or, what is the same in the terms used herein) basically elastic tubing means, and the proximal end of the probe projects into container means closed by locking means. The method comprises basically the following steps:
- stretching the flexible tubing means such that the proximal end of the invasive blood parameter probe slips essentially into the flexible tubing means,
- disconnecting the container means from the looking means,
- connecting the locking means with the distal end of the catheter, and
- releasing the flexible tubing means such that the proximal end of the invasive blood parameter probe projects into the catheter.

The invention makes use of additional tubing means the outside of which does not contact the patient's blood, and therefore its outside has not to be kept sterile. However, the tubing surrounds the sterile part of the probe, and thus its inside has to be sterile.

The proximal end of the probe projects into a container. Preferably, the container may at least partially be filled with a fluid. This is of importance in the case of an invasive blood parameter probe of the kind described above, as the probe tip has to be kept in a damp or aqueous embodiment during storage. However, this is not a mandatory requirement, as the present invention also relates to other kinds of invasive blood parameter probes, such as pressure sensors or the like. It also applies to blood parameter probes which are not of the fiber-optic type.

The sterile portion of the probe is thus completely embedded in the flexible tubing and the container, respectively.

It is understood that the probe should not be removed from the container, as its (sterile) proximal end could then contact non-sterile objects. Instead, the present invention proposes to stretch the flexible tubing. The proximal end of the probe slips now into the tubing, such that the container can be removed, whilst the proximal end of the probe does not project out of the tubing. Contact with nonsterile objects is thus impossible.

The locking means—which formerly closed the container—is now connected with the distal end of the catheter (which may already have been applied to the patient). As soon as the flexible tubing is released, the proximal end of the probe slips into the catheter and is thus ready for appliance to a patient.

The present invention has the particular advantage that no sterile part of the assembly may be touched, or come otherwise into contact with non-sterile objects. Handling and assembly are considerably improved and made easier, as no second person is required, and the assembling person does not have to take care of any projecting sterile portions of the probe which may come into contact with non-sterile objects.

Yet another considerable advantage of the present invention is easy manufacturing. In particular, plastic bags surrounding the probe are not required any more. This risk for the patient is also reduced by this measure, as the flexible tubing may not easily be damaged by external forces, as is the case with plastic bags.

Still another advantage of the inventive method, and/or of the related invasive blood parameter probe, is that the probe can be easily withdrawn into the catheter (even in use), in order to recalibrate it. Such recalibration is also a subject of the present invention; it covers basically a method for recalibrating an invasive blood parameter probe of the kind described herein, wherein the locking means is attached to a catheter, said method comprising the steps of:
  withdrawing the sterile probe portion into said flexible tubing means, and
  feeding a calibrating solution into said flexible tubing means.

The sterile probe portion may subsequently be pushed forward such that it projects out of the catheter again. Preferred calibrating solutions are solutions of NaCl (physiologic saline) or NaHCO$_3$.

The probe may also be withdrawn for the purpose of flushing with sodium chloride or a similar solution, in order to avoid clot formation.

In some applications, for example the fiber-optic probe described above, it is desirable to measure the invasive blood pressure as well. For this purpose, a pressure tube is provided. In a convenient and most advantageous embodiment of the present invention, the pressure tube is used as the flexible tubing means mentioned above. Such pressure tubes—which are, as such, known in the art provide the flexible characteristics desired for practicing the present invention; in particular, such pressure tubes are not subject to plastic deformation, but are rather deformed in elastic manner only. Another aspect of this embodiment of the invention is that the pressure tube serves two purposes, namely the sterile shielding of the probe, as well as invasive blood pressure measurement. It thus helps to save additional components, and manufacturing cost.

As already mentioned, the container is closed by locking means. Preferably, a threaded sleeve is used therefor. The container may thus be easily unscrewed from the sleeve, and the catheter may subsequently be screwed to the sleeve.

However, other locking means, e.g., a plastic cup snapped on the container or the catheter, respectively, may be used equally well.

In another preferred embodiment of the present invention, the invasive blood parameter probe includes a stop member attached to the distal end of the flexible tubing. This stop member may preferably be a Y-connector for connection of an invasive blood pressure monitor, in case invasive blood pressure monitoring is provided.

When a stop member of the kind described above is provided, the preferred method of practicing the present invention includes the step of
  spanning the flexible tubing means into or onto a spanning member such that the locking means abuts against a first stop of the spanning member, and the stop member abuts against a second stop of the spanning member.

According to this preferred method, the stretched flexible tubing is held in its position automatically by the two stops of the spanning member which engage with, or abut against, the stop member at the distal end of the tubing, as well as the locking means of the container. In other words, once the flexible tubing is stretched, it is held in place, such that the container may be easily removed and replaced by the catheter.

This latter feature makes handling further easier. However, it is noted that this is not a mandatory feature of the present invention—alternatively, the flexible tubing means may also be wound on a bar or the like, without additional stop members.

The spanning member may basically be of any suitable shape for providing the desired functionality. In one advantageous embodiment, it is a rigid body, e.g. manufactured from plastics. Preferred shapes are, for example, a U-like profile or a cylinder with a longitudinal slot. The two stops are provided by the front surfaces of the profiles.

Likewise, a rod may be used with additional projecting stops, wherein the flexible tubing extends parallel to the rod, and the stop member, as well as the locking means, are held outside of indentations through which the flexible tubing extends. A wheel with a circular groove may be used as well.

In another advantageous embodiment of the present invention, the spanning member is spring-loaded, wherein the spring is compressed prior to insertion of the probe, and the spring then stretches the flexible tubing automatically to its desired length. This embodiment has the particular advantage that spring stiffness may be selected such that the flexible tubing is stretched or expanded to a predefined length, and that the tubing may not be overstressed.

In still another preferred embodiment of the present invention, the step of releasing comprises the steps of
gripping the locking means as well as the stop member and
moving the locking means and the stop member away from each other until the spanning member is released.

That is, as soon as the catheter is fastened to the locking means, the flexible tubing is stretched such that the spanning member releases automatically, e.g., falls down in a table. Handling is thus very easy.

The invention also relates to an invasive blood parameter probe, in particular an invasive blood gas probe of the kind disclosed at the outset, comprising
a sterile probe portion attached to a non-sterile portion,
container means closed by a locking means, preferably a threaded sleeve,
wherein the proximal portion of the sterile probe portion projects into the container means, and
flexible tubing means, in particular a pressure tube, surrounding the sterile portion and attached to the locking means, as well as the non-sterile probe portion.

An invasive blood parameter probe of this kind is prepared for the above-described method, i.e., it can be spanned on a spanning member of the type discussed herein. The probe may further comprise a projecting stop member attached to the distal end of the flexible tube, wherein the stop member may preferably be a Y-connector for connection of an invasive blood pressure monitor.

The non-sterile probe portion may advantageously contain fiber-optic light guide means.

A spanning member for an invasive blood parameter probe, in particular for practicing the inventive method, comprises
a rigid and/or spring-loaded body,
a first stop for receiving locking means of a container into which the proximal end of the probe projects, and
a second stop for receiving a stop member attached to flexible tubing means surrounding a sterile probe portion.

Various preferred spanning members of this kind have been discussed above, and will be further discussed in the detailed description. Most preferably, the spanning member is basically defined by an open profile, e.g., a U-profile or a slotted cylinder.

It is understood and expressly noted that the present invention relates to all useful and novel combinations of the above disclosed features, whether alone or in any other or arbitrary combination.

BRIEF DESCRIPTION OF THE DRAWINGS

The invention will now be explained, by means of a non-limiting example, with reference to the accompanying drawings, in which.

DETAILED DESCRIPTION OF PREFERRED EMBODIMENTS

Figure 1:
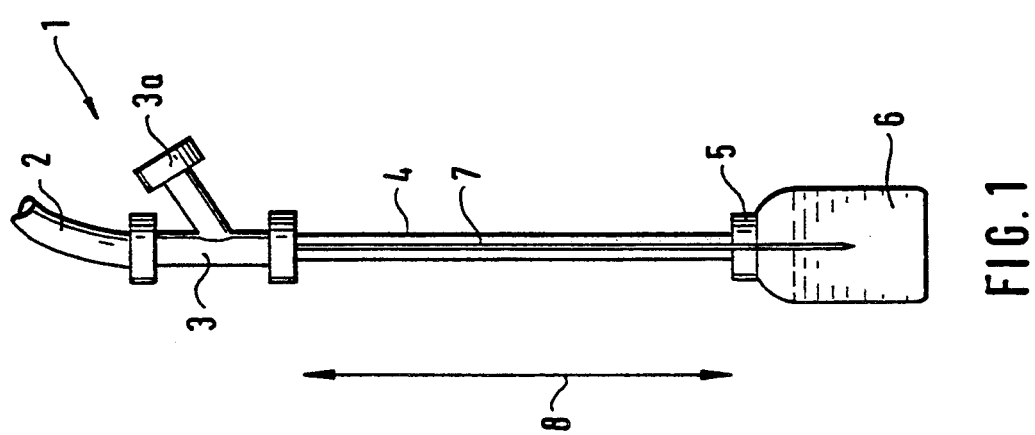
FIG. 1 depicts the basic configuration of an invasive blood parameter probe in its storage position.

In FIG. 1, an optical probe for the invasive measurement of blood parameters such as $pO_2$, $pCO_2$ or pH is generally designated as 1. A fiber-optic cable 2—which is in connection with an appropriate monitor, not shown—ends up at a Y-connector 3 (which is also used as a stop member, see discussion below).

A flexible pressure tube 4 is attached to Y-connector 3. The pressure tube is further attached to a threaded sleeve 5 which is screwed onto a fluid-filled container 6.

The outsides of all of parts 2–6 are non-sterile, as they are not intended for blood contact. Inside pressure tube 4 extends the sterile portion 7 of probe 1; its proximal end projects into the fluid in container 6. It is understood that portion 7, as well as the inside of pressure tube 4, and of container 6, are sterile.

FIG. 1 depicts the probe in its storage position. That is, the proximal probe tip is kept operative by the fluid in container 6. It has to be noted that the interconnections between fiber-optic cable 2 and Y-connector 3, as well as between Y-connector 3 and pressure tube 4 and sterile probe portion 7 are fixed. Joint 3a is provided for later connection of an invasive blood pressure monitor. It will be noted that no extra plastic bags or the like are required to keep the sensitive components of the probe sterile (although the present invention is not limited to an embodiment without such a plastic bag).

When the probe is prepared for introduction into a catheter, flexible pressure tube 4 is first stretched (i.e., made longer) as indicated by arrow 8. Dependent on the actual embodiment, either Y-connector 3 is moved away from sleeve 5 or vice versa. It is also possible to move both parts 3 and 5, e.g., by gripping the Y-connector as well as sleeve 5 (or container 6), and by moving both away from each other.

Figure 2:
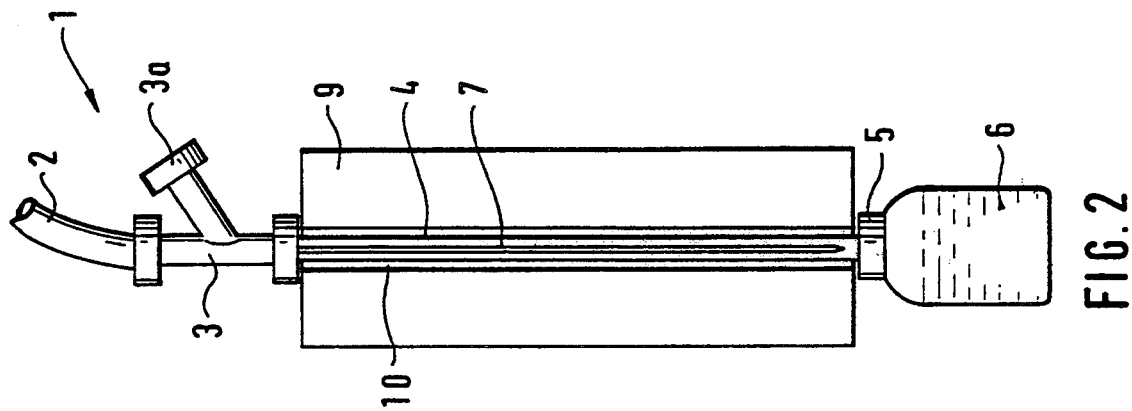
FIG. 2 depicts the step of stretching the flexible tubing by means of an appropriate spanning member.
Figure 5:
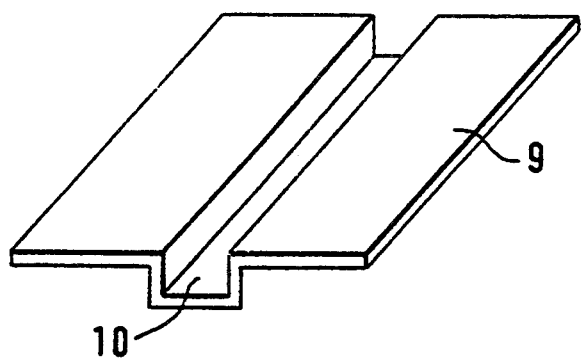
FIGS. 5–10 depict various spanning members.

The probe with stretched pressure tube is then inserted into a spanning member, as shown in FIG. 2. In this case, the spanning member is a U-shaped profile 9, as shown in more detail in FIG. 5. The pressure tube 4 containing sterile probe portion 7 is positioned in the U-shaped recess 10. FIG. 2 also shows that Y-connector 3, as well as sleeve 5, adjoin or abut against the front faces of spanning member 9. Further, due to the stretching of pressure tube 4, the proximal probe tip of sterile probe portion 7 has slipped into the interior of pressure tube 4, i.e., does not project into container 6 any more.

Thus, the probe tip does not project when container 6 is removed, e.g. by unscrewing. In fact, the catheter may now be connected (e.g., screwed to) sleeve 5, instead of container 6, without exposing any sterile component to non-sterile conditions. (In most cases, the catheter will already have been applied to the patient, prior to insertion of the invasive blood parameter probe.)

Figure 3:
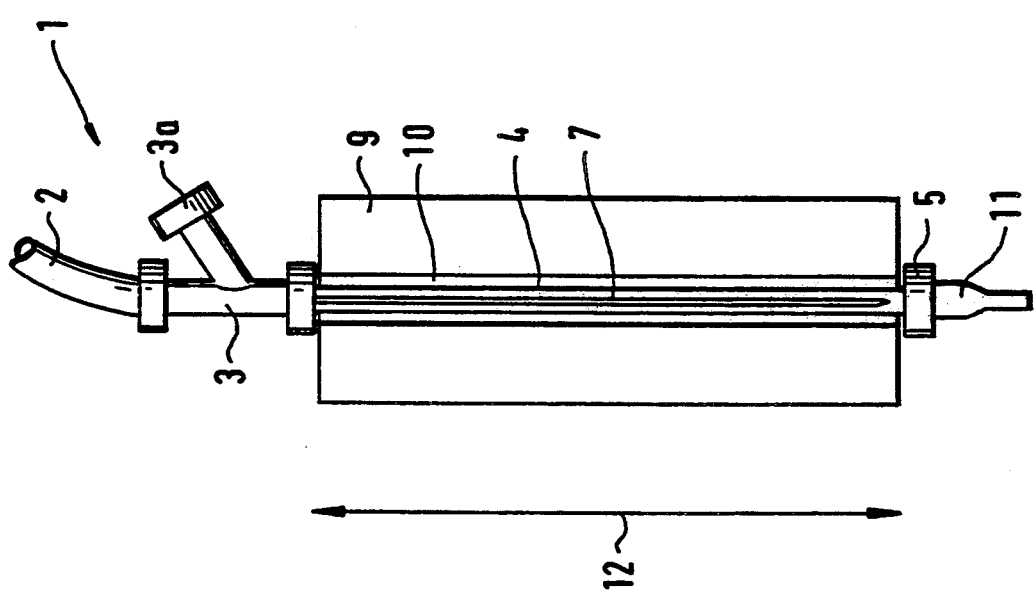
FIG. 3 shows the step of catheter connection.

The latter step of assembly is illustrated in FIG. 3. One will note that container 6 has been replaced by a catheter 11, wherein the probe tip is still protected by pressure tube 4.

If pressure tube 4 is now further stretched, for example by moving Y-connector 3 and sleeve 5 away from each other in their relative position, as indicated by arrow 12, spanning member 9 is released and may either be removed, or fall down on a table. This is illustrated by arrow 13 in FIG. 4.

Figure 4:
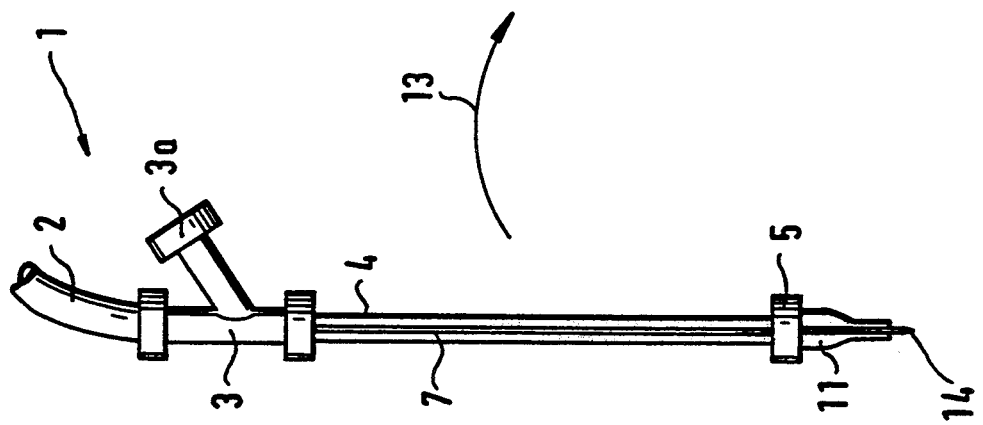
FIG. 4 depicts the probe and the catheter in their operating position.

FIG. 4 further shows that pressure tube 4 shrinks again to its original length as soon as no further expansion forces are applied to it. Thus, the proximal end of sterile probe portion 7 projects out of the catheter, as indicated by reference number 14. It will be appreciated that the catheter can already be positioned in the blood vessel of a patient, such that probe tip 14 is immediately in blood contact. Alternatively, probe tip 14 can also be withdrawn (into the interior of catheter 11 ) during the appliance of the catheter. Such withdrawal may also be useful for the purpose of catheter flushing, or for recalibration of the probe with a reference solution, as described above.

Figure 6:
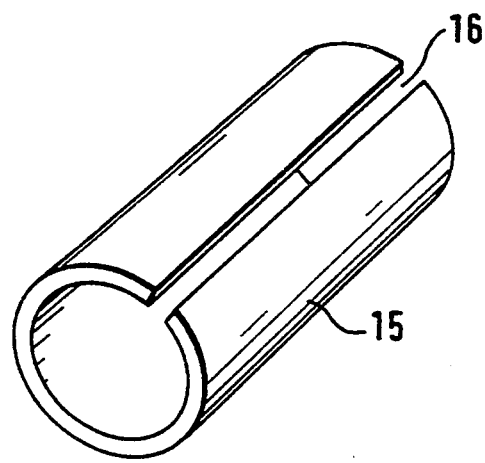

FIGS. 6–10 depict alternate embodiments of the spanning member. FIG. 6 shows a slotted cylinder 15 made from plastics, metal or any other suitable material. The pressure tube is introduced into the interior of the hollow cylinder through slot 16, and the Y-connector, as well as the sleeve, abut against the front faces of cylinder 15 in similar manner as in the embodiments of FIGS. 2 and 5.

Figure 7:
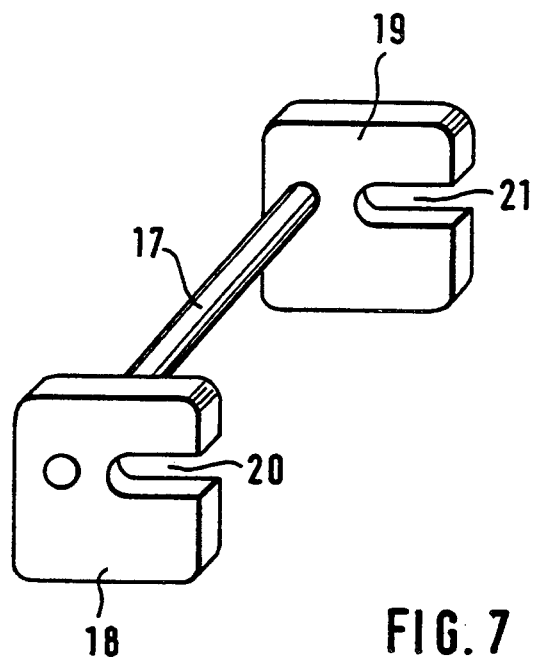

The spanning member in FIG. 7 consists of a rigid bar 17 which holds two rigid blades 18 and 19. Both of these blades include corresponding recesses 20 and 21 through which the pressure tube is introduced. The Y-connector, and the sleeve abut against the outer surfaces of blades 18 and 19.

Figure 8:
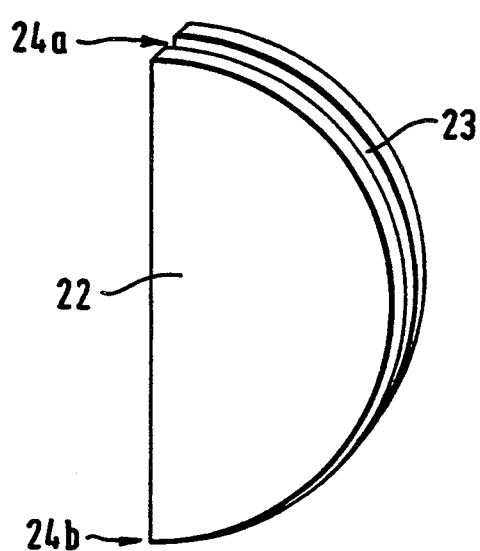

Still another spanning member 22 is shown in FIG. 8. It has the shape of a half circle including a groove 23 at its outer periphery. The pressure tube is introduced into this groove, and the Y-connector, as well as the sleeve, abut against the end portions 24a and 24b of the groove.

Figure 9:
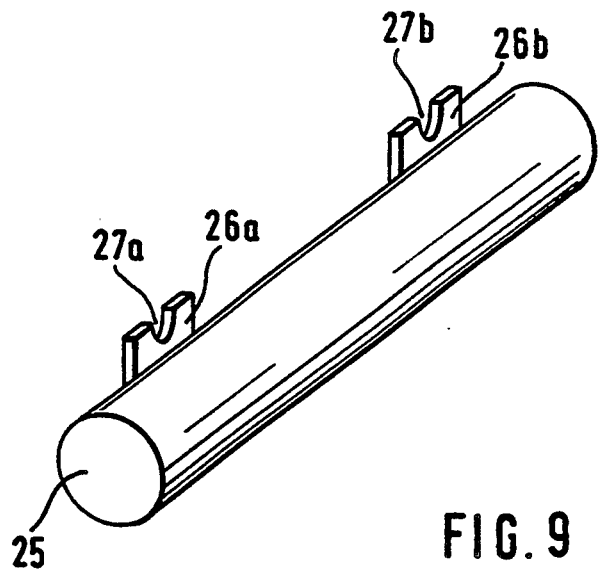

FIG. 9 shows a bar 25 on which the pressure tube may be wound. Projections 26a and 26b provide recesses 27a and 27b which serve as stop members for the Y-connector and the sleeve, respectively.

Figure 10:
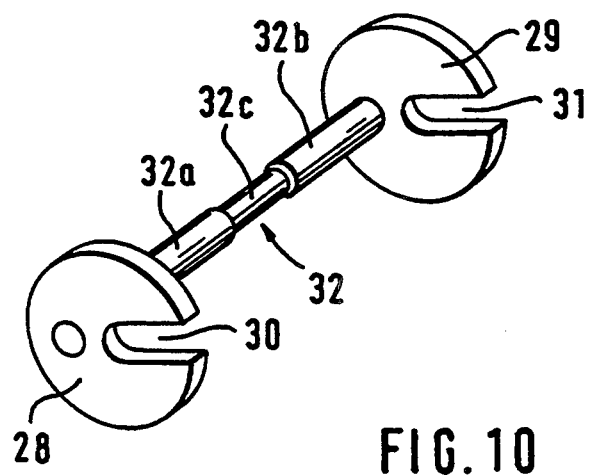

The spanning member in FIG. 10 is based on a different operating principle. Although blades 28 and 29 are similar to the blades in FIG. 7—these blades provide corresponding recesses 30.and 31—, bar 32 is of the telescopic type. In fact, it consist of bar portions 32a, 32b and 32c. Springs located in bar portions 32a and 32b exert pressure on mid portion 32c.

In operation, blades 28 and 29 are pressed—against spring force—in the direction against each other. The pressure tube is then introduced in recesses 30 and 31. Blades 28 and 29 are now released, such that they slide outwardly and span or stretch the pressure tube under spring force.

I claim:

1. Invasive blood parameter probe, comprising:
   - (4.1) a non-sterile portion and a sterile probe portion attached to the non-sterile portion,
   - (4.2) a container closed by locking means, (4.2.1) wherein a proximal portion of said sterile probe portion is projectable into said container, and
   - (4.2) flexible and stretchable tubing surrounding said sterile portion and attached to said locking means and said non-sterile probe portion, said tubing being sufficiently stretchable to permit said proximal portion of said sterile probe portion to slip into said tubing when said tubing is in a stretched position, said proximal portion slipping out of said tubing when said tubing is in an unstretched position.

2. Invasive blood parameter probe according to claim 1, wherein said container is at least partially filled with a fluid.

3. Invasive blood parameter probe according to claim 1, comprising a projecting stop member attached to a distal end of said flexible tubing.

4. Invasive blood parameter probe according to claim 3, wherein said stop member is a Y-connector.

5. Invasive blood parameter probe according to claim 3, further comprising a spanning member, wherein said spanning member comprises a rigid and/or spring-loaded body; a first stop for receiving said locking means of said container; and a second stop for receiving said stop member attached to said flexible tubing surrounding said sterile probe portion; and wherein said flexible and stretchable tubing is sufficiently stretchable to fit onto said spanning member.

6. Invasive blood parameter probe according to claim 1, wherein said non-sterile portion contains a fiber-optic light guide.

* * * * *